United States Patent [19]
El Hage

[11] Patent Number: 5,695,509
[45] Date of Patent: Dec. 9, 1997

[54] ASPHERICAL OPTICAL MOLDS FOR CONTINUOUS RESHAPING THE CORNEA BASED ON TOPOGRAPHICAL ANALYSIS

[76] Inventor: Sami G. El Hage, 5417 Delmonte, Houston, Tex. 77056

[21] Appl. No.: 401,967

[22] Filed: Mar. 10, 1995

[51] Int. Cl.$^6$ .................................................. A61F 9/00
[52] U.S. Cl. ...................... 606/166; 623/5; 351/161
[58] Field of Search ..................... 606/166; 623/4, 623/5, 6; 351/159, 160 R, 161

[56] References Cited

U.S. PATENT DOCUMENTS

| | | | |
|---|---|---|---|
| 3,212,097 | 10/1965 | Adler | 351/161 |
| 4,898,461 | 2/1990 | Portney | 351/161 |
| 4,952,045 | 8/1990 | Stoyan . | |
| 5,152,786 | 10/1992 | Hanna | 623/5 |
| 5,191,365 | 3/1993 | Stoyan . | |
| 5,196,027 | 3/1993 | Thompson et al. | 623/5 |
| 5,318,046 | 6/1994 | Rozakis | 606/166 |
| 5,349,395 | 9/1994 | Stoyan | 351/161 |
| 5,404,183 | 4/1995 | Seidner | 351/161 |

FOREIGN PATENT DOCUMENTS

1205907 A  1/1986  U.S.S.R. .................. 606/166

*Primary Examiner*—Michael Buiz
*Assistant Examiner*—Patrick W. Rasche
*Attorney, Agent, or Firm*—Merchant, Gould, Smith, Edell, Welter & Schmidt, P.A.

[57] ABSTRACT

Continuous, aspheric optical molds for reshaping the surface of the cornea having an inner concave surface matched to the topography of the cornea. The curvatures of the molds are modified from a curve matched to a patient's corneal topography to include a flattened pressure zone applying relative pressure and thereby displacing underlying corneal tissue, a steepened relief zone raised away from the surface of the cornea to receive displaced corneal tissue, and a flattened anchor zone to control and direct movement of displaced corneal tissue into the relief zones.

19 Claims, 3 Drawing Sheets

ASPHERICAL OPTICAL MOLDS FOR CONTINUOUS RESHAPING THE CORNEA BASED ON TOPOGRAPHICAL ANALYSIS

FIELD OF THE INVENTION

The present invention relates to a continuous, aspherical optical lens or mold and method for reshaping the cornea based upon corneal topography to effect correction of visual defects.

BACKGROUND OF THE INVENTION

Visual or optical defects which prevent parallel light rays entering the eye from focusing clearly on the retina exist in several varieties. In hyperopia (farsightedness), the point of focus lies behind the retina, generally because the axis of the eyeball is too short. In myopia (nearsightedness), the image is focused in front of the retina, generally because the axis of the eyeball is too long. In astigmatism, refraction is unequal on the different meridians of the eyeball, generally due to asymmetry in the shape of the eye.

Corrective glasses or contact lenses have been used to correct these defects, including convex (plus) lenses for hyperopia, concave (minus) lenses in myopia, and cylindric lenses in astigmatism. More recently, a surgical technique, myopic or hyperopic keratomileusis has been used to alter cornea curvature and thereby improve refractive error. This method cuts and removes a predicted thickness of the corneal disk with a microkeratome. Additional surgical procedures such as radial keratotomy use microincisions in the cornea to surgically modify the curvature of the cornea and thereby reduce or eliminate myopia or astigmatism.

Photorefractive keratectomy (PRK) uses a laser to ablate the center of the cornea and thus change the cornea. In Automated Lamilar Keratectomy (ALK) pressure is placed on the cornea to bulge the central dome. A flap in the dome is then opened, layers of corneal tissue are removed and the flap is then closed. Procedures combining aspects of ALK/PRK are sometimes used, called LASIK (laser in situ keratectomy).

While these surgical procedures effect long lasting correction of visual defects, they present an inherent risk of permanent damage to a patient's eye. However slight this risk might be, many patients are unwilling to undergo these surgical procedures to correct the curvature of the cornea. It would be of great utility to provide a non-surgical method for reshaping the cornea and thereby effecting correction of visual defects.

SUMMARY OF THE INVENTION

The molds and method of the present invention provide non-surgical reshaping and alteration of the curvature of the cornea. A continuous, aspherical optical mold according to the present invention, when applied to the cornea of a patient, exerts a selective pressure on the cornea causing displacement of corneal tissue away from a zone of applied pressure to a zone of relief, thereby reshaping the patient's cornea and improving the patient's vision without surgical intervention. In general, the design of the mold induces change in the corneal topography of the patient's eye to make a myopic eye more oblate or a hyperopic eye more prolate.

The continuous, aspherical optical molds according to the present invention are tooled in response to the specific contour or topography of a patient's cornea and to affect a desired reshaping or correction of the eye's curvatures.

When the mold is placed on the patient's cornea, a pressure zone of the mold exerts a relative selective pressure on the underlying or engaged region of the cornea to effect displacement of corneal tissue away from the region of pressure. A relief zone adjacent to the pressure zone does not contact the cornea and does not exert pressure on the cornea, but is an area where the mold is raised above the corneal surface. This area serves to receive corneal tissue which is displaced from the cornea underlying the pressure zone. An anchor zone adjacent to the relief zone and between the relief zone and the periphery of the mold controls or guides the reshaping of the corneal tissue, directing displaced tissue to the relief zone. The anchor zone also ensures good centration and maintenance of centration of the mold on the cornea thus providing predictability of the result and preventing overshooting the desired correction. The mold preferably contains a second relief zone or lift zone at its periphery.

A mold of the present invention useful in the treatment of myopia contains a central pressure zone, an adjacent annular relief zone, and an annular anchor zone adjacent to the relief zone and located between the relief zone and the periphery of the mold. When the mold is positioned on the patient's cornea, pressure is exerted by the central pressure zone on the approximate center of the corneal dome, thereby effecting displacement of corneal tissue away from the center of the dome and to the adjacent annular relief area. The pressure exerted at the anchor zone controls reformation of the corneal surface by guiding the displaced tissue into the relief zone. With time, the steep curvature of the myopic eye's corneal dome is flattened or reduced, and light incident over the central cornea will more correctly converge on the retina, thereby improving the patient's vision.

In the treatment of hyperopia, the pressure zone of the mold is positioned to apply pressure at the approximate mid-periphery of the patient's corneal dome, and the adjacent relief zone is centrally located. When the mold is applied to the patient's corneal surface, corneal tissue is displaced away from the mid-periphery and toward the relief area at the center of the dome, thereby increasing the steepness of the hyperopic eye's corneal curvature. In this embodiment, the pressure zone functions also as the anchor zone. The shape of the hyperopic eye is altered to a more prolate shape, permitting incident light to converge on the retina, and thereby improving vision.

To effect treatment of astigmatism where the patient's corneal dome has more than one curvature, each at a given axis, the mold's curvature places the pressure zone to apply pressure at the steepest meridian to effect its reduction and to minimize or eliminate differences in the curvatures. The characteristics of the mold for treating astigmatism are similar to those for a mold for correcting myopia.

In the method of the present invention, application of the aspherical optical molds to a patient's cornea results in reshaping of the cornea and provides improved visual acuity. In a preferred embodiment, once a patient's cornea has achieved an optimal shape, as determined by functional visual acuity, the mold of the present invention may be temporarily removed without loss of visual correction. It is appreciated that the reshaping of the cornea achieved by the method of the present invention is generally reversible, and will not persist indefinitely once molds are removed from the eye. However, it is contemplated that a patient may maintain the desired shape of the cornea by wearing the optical molds for a short period of time, e.g., approximately three to eight hours per day. For example, in some instances a patient may wear the molds one or two nights a week or every night during sleep to maintain the desired shape and functional vision.

DETAILED DESCRIPTION OF THE PREFERRED EMBODIMENT

Figure 1:
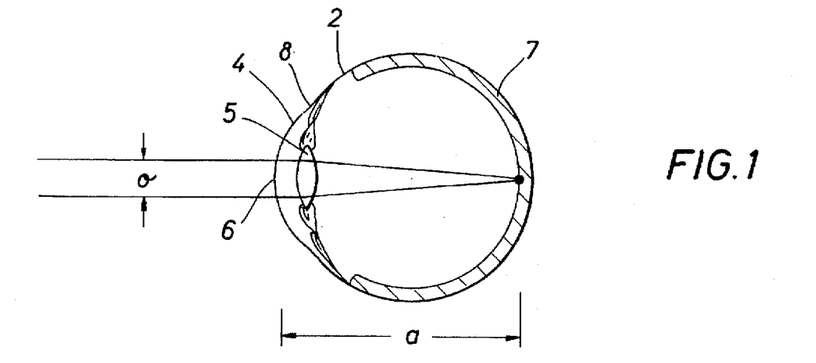
FIG. 1 is a schematic diagram of an average, normal eye, side view, in cross-section.

A continuous, aspherical optical mold of the present invention has a specific shape and contour determined by the corneal topography of the eye to be treated and the corneal reshaping desired. Referring to FIG. 1 the normal eye contains a cornea 2. The portion of the cornea 2 which projects over the lens 5 is termed the corneal dome 4. The corneal dome 4 is generally considered rotationally symmetrical and aspherical in shape, with the approximate dome center 6 having essentially the highest projection away from the center of the eye. A generally circular optical zone o transmits incident light which normally converges on the retina 7.

Figure 2:
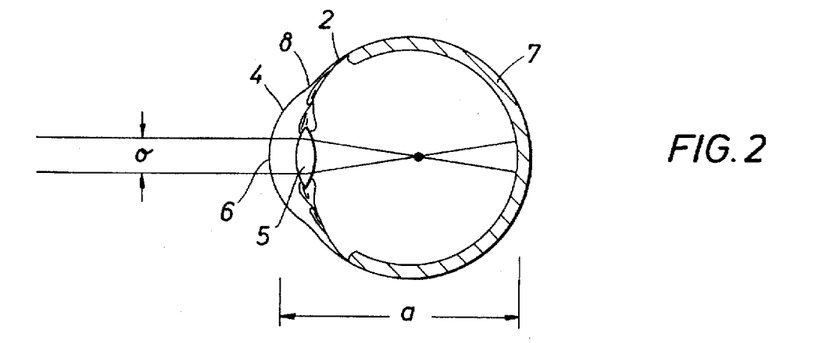
FIG. 2 is a schematic diagram of a myopic eye in cross-section.
Figure 3:
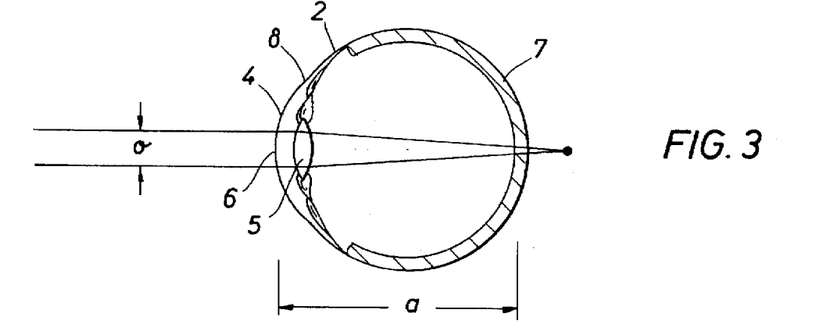
FIG. 3 is a schematic diagram of a hyperopic eye in cross-section.
Figure 4:
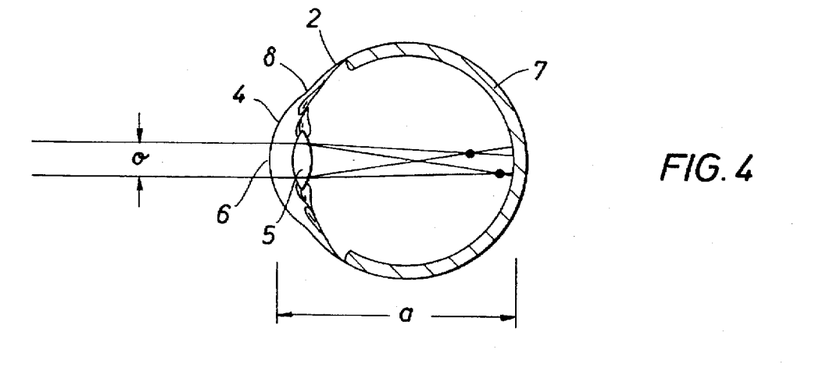
FIG. 4 is a schematic diagram of an astigmatic eye in cross-section.

Defects in visual acuity are correlated with distortions in the shape of the cornea. As shown in FIG. 2, convergence occurs in front of the retina in a myopic eye (nearsighted), and is associated with an elongated axis $\alpha$ and a steepened or heightened corneal dome 4. The opposite is true in a hyperopic eye, where the corneal dome 4 is flattened or depressed, and the axis $\alpha$ of the eye is shortened. As shown in FIG. 3, convergence in the hyperopic (farsighted) eye occurs beyond the retina 7. In an eye having astigmatism, multiple curvatures of the cornea cause multiple areas of convergence as shown in FIG. 4.

The degree of corneal distortion and precise location and size of a patient's corneal dome center 6 and dome periphery 8 may be determined by one of skill in the art using a videokeratoscope or corneal topographer. As described in pending U.S. application Ser. No. 08/046,619, measurements of the contour of the cornea of the human eye have been used to facilitate the design and fit of contact lenses, as well as for use and performance of surgical procedures.

In a conventional videokeratoscope used to measure the cornea, concentric rings of light from a source of light within a housing are directed onto a cornea and reflected by the cornea onto the film of a camera as an image of the rings. The deviation of the rings from their known concentricity is measured and this data is processed mathematically to determine the actual contour of the cornea, which is not a perfect sphere and which differs from one individual to another. Conventional photokeratoscopes are disclosed, for example, in U.S. Pat. Nos. 3,248,162 and 3,598,478. Videokeratoscopes or corneal topographers are disclosed for example, in U.S. Pat. Nos. 4,978,213, 5,227,818 and U.S. patent application Ser. No. 08/046,619. In general, a corneal topographer includes a camera means, such as a charged coupled device camera system for sensing the images of rings of light reflected from the cornea. The camera apparatus sends standard video signals to a computer, such as a conventional, commercially available image processor, which digitize the video signals. The computer analyzes the digital data and produces data useful in determining the contour of the cornea of the human eye. A corneal topographer apparatus which automatically centers and focuses the corneal image reflected from a patient's cornea onto a charge coupled device camera system is disclosed in U.S. patent application Ser. No. 08/046,619.

Any of the above-described methods, as well as others known to those of skill in the art, may be used to determine the topography of the cornea of a patient to be fitted with an optical mold of the present invention. Whatever method is utilized, the data is analyzed to determine the corneal condition, e.g., regular, irregular, or astigmatism by methods generally known in the art. The location and curvature of the corneal dome 4 and center 6 is determined. Using these measurements, as well as the degree of refractive error to be corrected, a mold or lens of the present invention is machined to apply selective pressure to areas of the patient's cornea in order to effect a desired displacement and reshaping of the cornea. Reformation or reshaping of the patient's cornea results in improvement of the patient's vision.

Figure 5A:
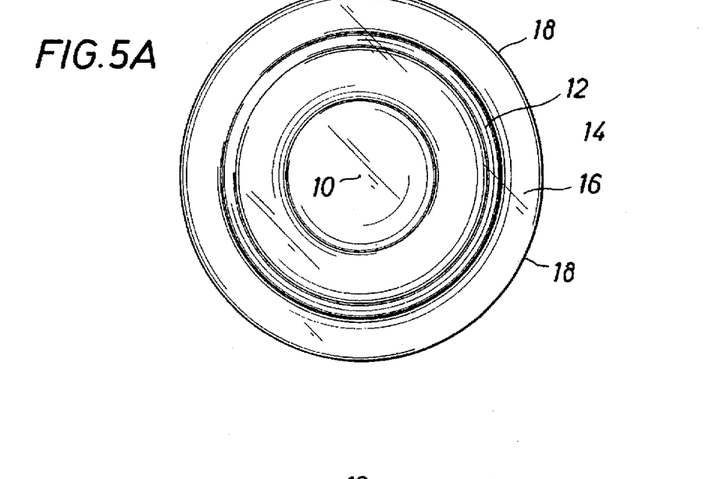
FIG. 5A is a schematic diagram, top view, of a mold of the present invention appropriate for treating the myopic eye of FIG. 2.
Figure 5B:
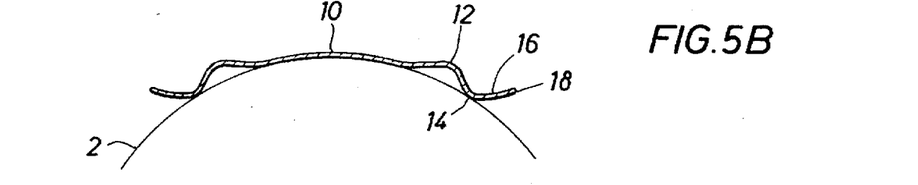
FIG. 5B is a schematic diagram, exaggerated in detail, of the mold of FIG. 5A in cross-section.
Figure 6A:
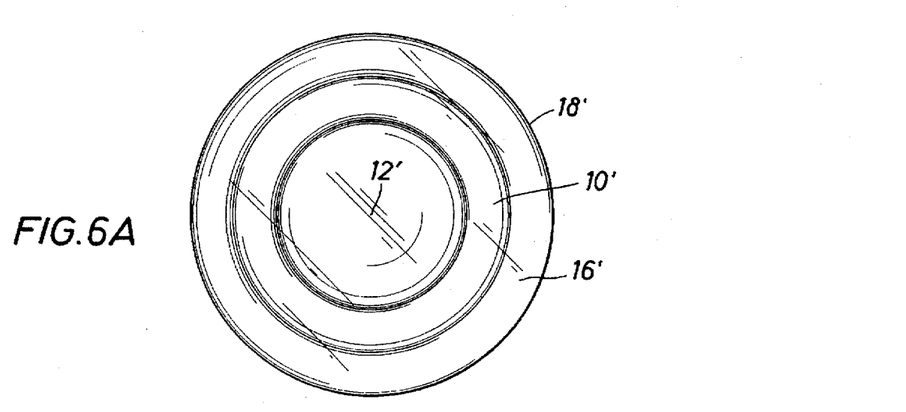
FIG. 6A is a schematic diagram, top view, of a mold of the present invention appropriate for treating the hyperopic eye of FIG. 3.
Figure 6B:
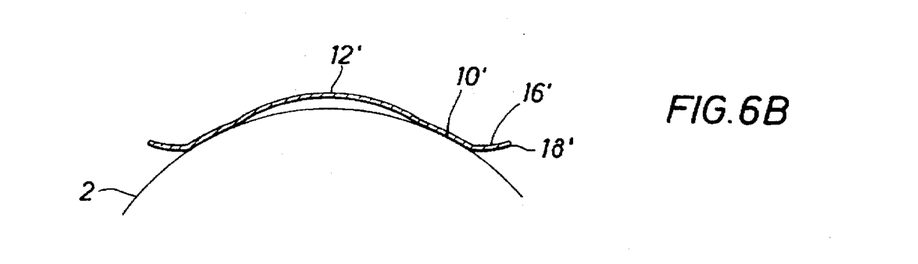
FIG. 6B is a schematic diagram, exaggerated in detail, of the mold of FIG. 6A in cross-section.

The contour and shape of the optical molds of the invention are diagrammatically shown in FIGS. 5A, 5B, 6A, and 6B. FIGS. 5A and 5B show the general design of molds for treating myopia or astigmatism. FIGS. 6A and 6B show the general design of molds for treating hyperopia. FIGS. 5B and 6B diagram the molds in cross-section, with the dimensions greatly exaggerated to explain the design. In general, and as shown in FIGS. 5A, 5B, 6A and 6B, the contour and shape of the optical mold of the present invention will include a pressure zone 10, 10' which will overlay or engage a region of the corneal surface where reduction is desired. When the mold is placed on the eye, the pressure zone 10, 10' will apply a relative pressure to the underlying or engaged region of the cornea. It is understood that the mold is separated from the cornea by fluid, e.g., tears present between the mold and the surface of the cornea but the fluid follows the contour of the cornea.

The mold of the present invention also includes a relief zone 12, 12'. The relief zone 12, 12' is an area adjacent to the pressure zone 10, 10' that creates a space or void between the surface of cornea and the mold. No pressure is applied from the relief zone 12, 12' onto the underlying region of the cornea. In contrast to the pressure zone 10, 10', the area between the relief zone 12, 12' and the underlying corneal surface is sufficiently spacious to receive corneal tissue displaced by pressure applied at the pressure zone 10, 10'. An annular anchor zone 14 is located adjacent to the relief zone 12. The anchor zone 14 is in contact with the cornea and exerts minimal pressure on the cornea for purposes of anchoring the mold on the corneal surface to achieve and maintain good centration. By applying relative pressure adjacent to the relief zone 12, the anchor zone 14 guides the displaced corneal tissue into the area under the relief zone 14.

The position of the pressure zone 10 on the cornea is important to the mold's function of providing useful reshaping of the cornea. Referring to FIG. 5A, in a mold designed to treat myopia, the pressure zone 10 is positioned to apply pressure at the approximate center of the corneal dome. Referring to FIG. 6A, in a mold designed to treat hyperopia, the pressure zone 10' is positioned to apply an annular pressure that will evenly heighten the corneal dome and serve the function of both pressure and anchor zones. The anchor zone 14 maintains the mold's position on the cornea and controls the direction of corneal tissue displacement into the area of relief. The location of the anchor zone 14 also provides a feedback mechanism for viewing the mold's centration on the corneal surface by topography. These control mechanisms permit efficient and controlled reformation of the cornea and help to prevent overshooting the desired correction which might otherwise occur.

Preferably, the mold of the present invention includes a second annular relief zone 16, 16' at the periphery 18, 18' of the mold. The second relief zone 16, 16' is raised away from the cornea 2, 2', e.g., to approximately 80–100 microns at the periphery 18, 18' of the mold, to assist in the movement of fluid and nutrients under the mold, and also to permit easy removal of the mold from the eye.

The specific location and size of the pressure zone, relief zone, anchor zone, and second relief zone will differ with the specific condition of the patient's eye and corneal topography, and with the type of correction desired. In general, molds useful for the treatment of myopic and astigmatic conditions will have similar features and those useful for hyperopic eye conditions will have similar features.

To affect specific alterations in the shape of the cornea, for example, correcting the general topography defects shown in FIGS. 2, 3, and 4, a continuous aspherical mold is constructed having specific curvatures which will exert relative pressure on regions of the cornea in need of reduction or flattening. The mold also contains regions recessed away from the cornea to accept displaced corneal tissue. As shown in FIG. 5A, a mold for reshaping the myopic cornea of FIG. 2 includes a generally circular periphery 18 defining the edge of the mold; a generally circular pressure zone 10 to overlay and engage the approximate center 6 of the corneal dome 4; and an annular relief zone 12 positioned adjacent to the pressure zone 10 approximately at the mid-periphery of the mold. An annular anchor zone 14 is positioned adjacent to the relief zone 12 and between the relief zone 12 and the periphery 18, and a second release zone 16 is preferably positioned at the periphery of the mold 18.

As shown in FIG. 5B, when the mold is applied to an eye, the pressure zone 10 engages the underlying corneal tissue. "Engages" means that portion of the mold is separated from the corneal tissue essentially only by tear fluid, and the "engagement" causes pressure to be exerted by the pressure zone 10 of the mold onto the underlying corneal tissue. The pressure applied at the pressure zone 10 causes the underlying cornea to be displaced away from the region of applied pressure.

The relief zone 12 is that portion of the mold which, when positioned on an eye, does not "engage" the underlying cornea, but in contrast, is recessed or raised away from the cornea, creating an annular space or zone between the mold and the corneal surface for receiving displaced corneal tissue.

When the mold is applied to an eye, the annular anchor zone 14 engages the underlying cornea. The anchor zone 14 exerts a minimal pressure on the corneal surface underlying the mold at a location adjacent to the relief zone 12 and between the relief zone 12 and the periphery 18. The pressure exerted by the anchor zone 14 cooperates with the central pressure zone 10 and guides displaced corneal tissue into the space underlying the mold at the relief zone 12. Pressure exerted by the anchor zone 14 also stabilizes the mold on the corneal surface and permits achievement and maintenance of good centration of the mold on the cornea. A second release zone 16 is preferably positioned at the periphery 18 of the mold. Like the release zone 12, the second release zone 16 does not engage the underlying cornea. The second release zone 16 facilitates easy access of fluid and nutrients under the mold and also permits easy "lift off" or removal of the mold from the corneal surface. In general, the periphery 18 of the mold has a sufficient curvature to be raised away from the cornea for access of fluids, e.g., approximately 80–100 microns, and preferably about 90–100 microns.

A mold for correcting hyperopia, in a similar manner as described above for the general design of a mold to correct myopia, but having an opposite purpose and therefore construction, is shown in FIGS. 6A and 6B. The annular contact zone 10' is positioned generally to overlay the periphery of the corneal dome 4, with the circular release zone 12' central to the annular pressure zone 10', and positioned generally to overlay at least the approximate center 6 of the dome 4. A second release zone 16' is preferably located at the periphery 18' of the mold. The periphery 18' is preferably raised approximately 80–100 microns from the corneal surface, as described above.

The design of a mold to correct astigmatism of the eye of FIG. 4 is in general similar to the mold of FIGS. 5A and 5B for treating a myopic eye. The contact zone 10 is centrally positioned in the mold to overlay the heightened region of the cornea in need of reduction. Relief zone 12 is positioned adjacent to the pressure zone 10, and anchor zone 14 is positioned adjacent to the relief zone 12.

The concave surface of the molds of the present invention are formed with a continuous aspheric curvature from center to periphery, that is, with a gradual change of curvature into each specified zone. The continuous curve is achieved by machining the mold in accordance with a mathematical analysis of the best curve fit for the desired distances of the mold from the surface of the cornea at each of the specified zones.

The molds of the instant invention may be fabricated from materials and using methods known to be useful, for example, in the manufacture of contact lenses. Such materials include those useful in fabricating gas (oxygen) permeable contact lenses, e.g., fluroperm (Paragon Optical Co.)

or any oxygenated rigid plastic available and known to be useful in fabrication of contact lenses. An especially preferred lens material is fluroperm 60 or 90, because it has high DK value (oxygen transmissibility). In a preferred embodiment, the molds will also have optical properties to correct refractive error during the reshaping of the cornea.

The molds of the present invention are machined to provide the appropriate reshaping of a particular patient's eye. The eye's corneal topography is defined and mapped using conventional corneal topography equipment as described above. The refraction of the eye is measured by conventional techniques. A diagnosis of the condition to be treated is made, e.g., myopia, hyperopia or astigmatism and the amount of refractive error is determined. The patient's corneal topography is analyzed to select the appropriate parameters for the patient's mold, including the position, size and location of the corneal dome, the shape factor (e.g., deviation from a perfect sphere), and curvatures of the mold to match the patient's topography.

Measurements of a patient's corneal topography are adjusted for the desired correction and used to specify the dimensions of the corrective mold. For the myopic eye shown in FIG. 2, the approximate size of the optical zone o, or heightened area of the corneal dome is measured as the radius (or diameter) from the approximate center of the dome 6 to the approximate mid-periphery 8. Generally, for a mold having a total diameter of about 10 mm, the diameter of the optical zone will vary from about 4 to about 7.5 mm. An area within the patient's optical zone o is analyzed to determine the average curvature of the optical zone, $R_o$, which determines the base curvature of the corrective mold. As shown in FIGS. 5A and 5B, the relative size and position, e.g., annular diameters of the pressure zone 10 and the curvature and annular diameter of the relief zone 12 is determined in part by the correction needed and the aggressiveness of the desired therapy. In general, the smaller the diameter of the pressure zone 10, the more aggressive the therapy. A smaller diameter pressure zone 10 exerts greater pressure on the underlying cornea, and a greater curvature is needed in the relief zone 12.

The desired curvature of the pressure zone 10 is calculated to apply a relative pressure to the underlying cornea according to the refractive error to be corrected, and is generally calculated as the base curve plus d where d is a conversion factor determined by the refraction of the eye. The value of d is about 0.2 mm per diopter of correction. For example, the conversion factor may be as shown in the following table.

| Eye refraction (diopters) | Pressure zone (mm diameter) | d (mm) |
| --- | --- | --- |
| 5.5–6 | 4–5.0 | 1.2 |
| 4–5 | 5–5.5 | 0.8–1.0 |
| 3–4 | 5.5–6.0 | 0.6–0.8 |
| 1–3 | 6.0–6.5 | 0.2–.6 |

The curvature of the annular relief zone 12 extends continuously from the periphery of the pressure zone 10 to the adjacent anchor zone 14, generally about 0.5–1 mm across the annular radius (1.0–2.0 annular diameter) of the mold. Its curve is generally the base curve minus d, in order to create a spacious area under the mold to accept displaced corneal tissue.

The curvature at the anchor zone 14 is machined to provide a parallel fit, that is, to contact or engage the underlying cornea. The curvature at the anchor zone 14 will thus be generally the same as at the pressure zone.

The mold then is machined to provide a continuous curvature from the annular anchor zone 14 through the second release zone 16 to the raised periphery 18 of the mold. The periphery 18 of the mold is machined to be raised approximately 80–100 microns from the surface of the cornea to provide edge lift.

In general, the mold for treating a myopic cornea will have a total diameter of approximately 9.0–11.0 mm (4.5–5.5 mm radius), preferably about 9.5–10.5 mm (4.75–5.25 mm radius), and most preferably will be about 10 mm (5 mm radius). As shown in FIG. 5A, this includes approximately 4–7.5 mm central diameter cd (2–3.75 mm radius) of a central pressure zone, preferably 4.5–6.0 mm diameter (2.25–3.0 mm radius), and approximately 12.5 mm diameter annular radius r of relief zone, with approximately 0.5–3.5 mm annular radius r2 for anchor zone and second release zone.

In preparing a mold for the treatment of a hyperopic cornea as shown in FIGS. 6A and 6B, the location and size of the patient's optical zone o and its periphery is first determined, and the base curve and desired curvature at each zone of the mold calculated as described above for a mold to treat myopia. The average curvature of the patient's optical zone, e.g., over about 5 mm central diameter (2.5 mm radius) is calculated, and approximately 0.2 mm per diopter of correction required (at) is added to determine the base curve of the pressure zone. The annular radius r' of the pressure zone 10' is about 1–2.5 mm.

A steepened curvature over the center of the mold creates the relief zone 12', generally the base curve minus d, having a central diameter cd' of about 4–7.5 mm. The periphery 18' of the mold is machined to be raised above the curvature of the cornea approximately 80–100 µ, and preferably about 90 microns.

As described above for the mold to treat a myopic eye, the curvature of the mold to treat the hyperopic eye is continuous, flowing gradually from the center of the relief zone 12', through the pressure zone 10' and from the pressure zone 10' to the periphery 18' of the mold.

The method of forming a mold for the treatment of astigmatism is similar to that for forming a mold to treat a myopic eye. The general diameter and average curvature of the optical zone is determined. Next, the curvature of the pressure and release zones are calculated, as well as the anchor zone and secondary release zone curvatures.

The specific curvature of each mold is determined from the topography of the eye and the desired level of visual correction needed. One general method for calculating the curvatures of a mold for treating a myopic eye is described below. It is understood that several methods may be used to achieve a mold of the present invention. Thus, the following description is meant to be exemplary, and does not limit the invention.

First, the patient's corneal topography is measured. Examining a central portion of the cornea, e.g., the optical zone at approximately 4–5 mm central diameter (about 2–2.5 mm central radius), an average "shape factor" is calculated. The shape factor indicates the cornea's deviation from a perfect sphere and is calculated by the formula:

$$p_n = \frac{2R_o x_n - y_n^2}{x_n^2}$$

where:

$x_n$ = sagittal depth of the semi-meridian (n)

$y_n$=length of the semi-meridian $R_o$=radius of curvature of the corneal center (e.g., 2 mm central radius)

A shape factor (ρ) is calculated for a number of multiple semi-meridians 360° about the central axis of the cornea. For example, ten (10) semi-meridians may be analyzed spaced approximately 36° apart. Thirty-six (36) semi-meridians may be analyzed spaced 10° apart. Alternatively, 360 semi-meridians may be analyzed spaced 1° apart. After determining the shape factor (ρ) at each semi-meridian analyzed, an average corneal shape factor ($ρ_0$) is calculated.

Next, the base curve of the mold is calculated as the $R_o$ to which a conversion factor, d, is added. As described above on pages 14–15, d relates to the amount of visual correction required, and is approximately 0.2 mm per diopter of correction. For example, if the calculated $R_o$ of the cornea is 8.0 mm and the desired visual correction is 3 diopters, the calculated base curve of the mold is 8.0+3(0.2)=8.6 mm.

The desired sagittal height (S) of the cornea and of the mold to be applied to the cornea, that is, the height of the curvature, is next determined using the formula:

$$S = R - \sqrt{(R^2 - y^2)}$$

where

S=sagittal height

R=radius of curvature y=length of the semi-meridian

The sagittal height is calculated both before corneal correction ($S_n$) and after application of the mold for the desired correction ($S_c$), recognizing the application of the mold will alter the sagittal height of the cornea. The difference between $S_n$ and $S_c$ indicates the amount of change in the shape of the cornea upon application of the mold, which is generally about 10 μ per diopter.

In the example discussed above, an optical zone of approximately 5.0 mm diameter (2.5 mm radius) having a base curve of 8.0 mm and a desired correction of 3 diopters (0.2 mm×3 diopter =0.6 mm) will have a base curve of 8.6 mm. Calculating $S_n-S_c$, a difference of 29 μ is the sagittal distance the cornea will be depressed at the contact zone.

$$S_n = 8.0 - \sqrt{(8.0)^2 - (2.5)^2} = 0.40060 \text{ mm}$$

$$S_c = 8.6 - \sqrt{(8.6)^2 - (2.5)^2} = 0.37139 \text{ mm}$$

$$S_n - S_c = 0.029 \text{ mm} = 29\mu$$

Figure 7:
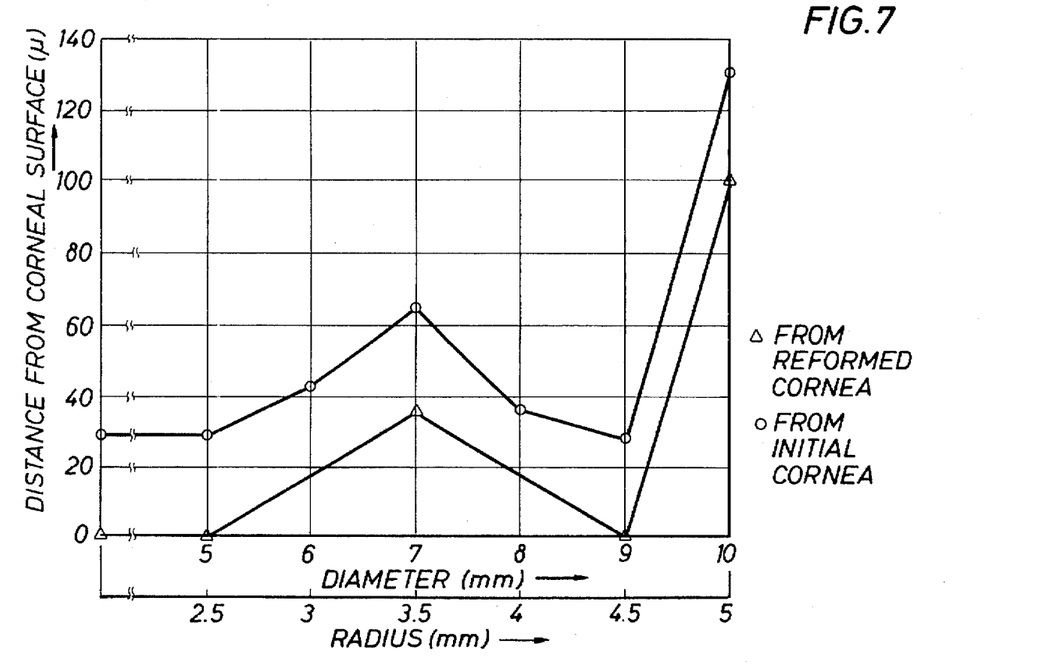
FIG. 7 is a graph showing calculated points of a mold's curvature at each of the zones of a mold formed to treat a myopic or astigmatic eye. The radius of the mold is shown in the x axis in mm, with the y axis showing the distance of the applied mold from the surface of the cornea. Circles represent distances of the mold from the non-reformed corneal surface and X's represent distances of the settled mold from the surface of the reformed cornea.

Therefore, at the pressure zone the mold will engage the cornea and when settled, that is, after reformation has occurred, the mold will have caused the cornea to be depressed by about 29 μ. This is represented in FIG. 7 where each circle represents the distance of the mold from the corneal surface at time of application and each X represents the desired distance of the mold from the corneal surface after the mold has settled and reformation is achieved. At the pressure zone, e.g., 0–5 mm diameter (0–2.5 mm radius), 0 μ is the distance between the settled mold and the reformed surface of the cornea (X) and 29 μ is the initial distance (●), e.g., from the central axis of the cornea and extending radially for about 2.5 mm to the periphery of the relief zone.

The relief zone for this example mold treating myopia is an annular ring having its highest point centered at about 3.5 mm radius (7.0 mm diameter). The relief zone's highest point from the corneal surface is minimally calculated as the sum of the expected mount of displaced corneal tissue plus the amount the corneal surface is displaced. To accommodate the displacement of corneal tissue away from the pressure zone, in general, the mold preferably is raised from the reformed corneal surface about 12 μ per diopter of correction. In our example with correction of 3 diopters, the settled mold is raised about 36 μ from the reformed corneal surface. Since the surface of the cornea will be depressed 29 μ by the application of the mold (more or less 10 μ per diopter), this 29 μ is added to the desired 36 μ to yield an initial high point of the mold's release zone of approximately 65 μ from the initial corneal surface.

The anchor zone is generally positioned at about 4.5 mm annular radius of the 10 mm diameter mold and places the mold in pressure contact or engaged fit with the corneal surface. This is shown in FIG. 7 as 0 μ between the settled mold and the surface of the cornea, or 29 μ for the initial mold at approximately 9 mm annular diameter (4.5 mm annular radius).

The periphery or lateral edge of the mold forms the highest point of the secondary release zone, which in the settled mold, is preferably raised from the surface of the reformed cornea about 90–100 μ or about 129 lμ in the initial mold. This coordinate is shown in FIG. 7 as the edge of the mold at about 10 mm annular diameter (5.0 mm annular radius) having a distance from the reformed corneal surface of about 100 μ for the settled mold or about 129 μ from the initial corneal surface.

These desired coordinates are then used to determine the curve which best fits an optical polynomial equation, for example as follows:

$$X = cy^{2'}[1 + \sqrt{(1 - \rho c^2 y^2)}] + A_4 Y^4 + A_6 Y^6 + A_8 Y^8 + A_{10} Y^{10} + A_{12} Y^{12} + A_{14} Y^{14}$$

where:

$c=1/R_o$ $R_o$=radius of curvature of the corneal center (e.g., 2 mm central radius)

ρ=shape factor y=length of semi-meridian

Preferably, additional points are added to soften the slope of the change in curvature. For example, as shown in FIG. 7, the slope of the change of curvature from 0 μ at 2.5 mm radius to 36 μ at 3.5 mm may be softened by placing a point at about 3.0 mm about midway between the flanking points, e.g. about 43 μ. Additionally, the descent from 36 μ at the 3.5 mm release zone to 0 μ at the 4.5 mm anchor zone may be steepened near the anchor zone by placing a point at about 4.0 mm having a distance of about 15 μ.

Figure 8:
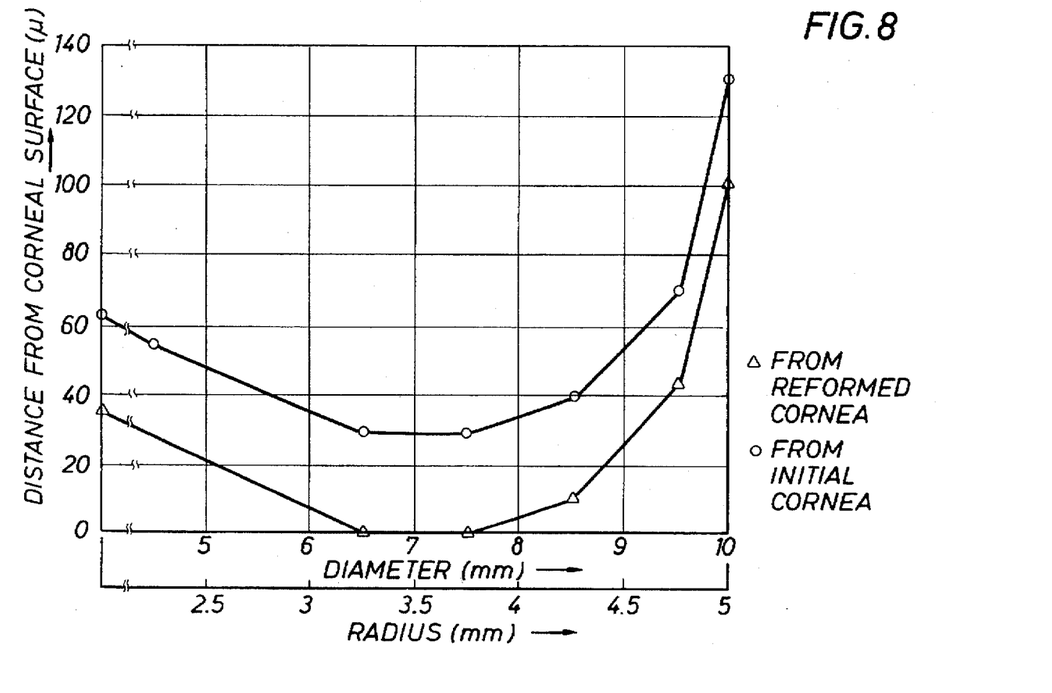
FIG. 8 is a graph showing calculated points of a mold's curvature at each of the zones of a mold the invention formed to treat a hyperopic eye. The radius of the mold is shown in the x axis, with the y axis showing the distance of the mold from the surface of the cornea. Circles represent distances of the mold from the non-reformed corneal surface and X's represent distances of the settled mold from the surface of the reformed cornea.

The preparation of a mold for the treatment of a hyperopic eye would follow a similar calculation scheme, but the representative points would differ with the opposite purpose of the curvatures (see FIG. 8). A mold for the treatment of hyperopia generally contains a pressure zone located in an annular ring at about 6.5 to about 7.5 mm annular diameter (3.25 to about 3.75 mm annular radius) of a 10 mm diameter mold. At this pressure zone, the mold engages underlying the corneal surface, as shown by 0 μ distance from the reformed surface of the cornea of the settled mold or 29 μ in the initial surface at this radius in FIG. 8. The highest point of the release zone is positioned at the central axis, e.g., 63 μ at 0 mm. The periphery of the mold at about 10 mm diameter (5 mm radius) is similarly raised 90–100 μ away from the surface of the reformed cornea (129 μ from the initial surface) for edge lift. Additional points can be used to soften the change in slope, for example, to prolong the height of the central release zone by placing a height of about 55 μ at about 2.0 mm radius. Likewise, a quick rise to the secondary release zone at the periphery of the mold may be accentuated by placing additional points closer to the surface of the cornea at about 4.25 and 4.75 mm radius. The coordinates (x,y) are used to generate a polynomial fit defining the multiple curvature of the mold of the instant invention.

In a preferred method for producing the molds of the invention, a computer software program takes the input of a patient's corneal topography, calculates the average shape factor, takes the input of the diopter correction desired, total diameter of the mold, and the desired x,y points of the pressure zone, relief zone, anchor zone, secondary relief zone, and periphery zone and generates the needed coefficients. The software program also permits insertion of additional x,y points as described above to change the slope of the changes in curvature as desired. The program then calculates the polynomial fit, resulting in a formula for the multiple curvature of the continuous aspherical mold. In the most preferred embodiment, this equation is directly transferred to a lathe which can interpret the equation and transform the data into continuous cuts in a lens blank which form the mold of the invention.

The molds and methods of the present invention provide corrective molds to reshape a patient's cornea that are specifically designed to the patient's corneal topography. The precise amount of correction needed is known and directly correlated to the shape and size of the mold. The instant invention prevents overcorrection or overshooting the desired treatment in contrast to methods of reshaping currently available. The instant molds and methods are designed to fit the aspheric surface of an individual's cornea, thus providing a better fit and a more precise correction of defects. The method of producing the molds provides for a continuous aspheric surface which does not cause discomfort to the patient, and which is anchored on the cornea for good centration, yet can be easily lifted from the surface of the eye.

In the method of the present invention, the curvature of the cornea is altered or reshaped to correct visual defects. The reshaping or alteration of the cornea is achieved without surgical intervention. A mold of the present invention is specifically designed to effect treatment for a specific patient's eye. The patient applies the mold generally as a typical contact lens would be applied or worn.

In general, after the patient has worn a mold of the present invention for a period of time, the patient is monitored to record progress in reaching an optimal shape or optimal level of correction. For example, the patient may be monitored approximately weekly or monthly by measuring corneal topography and comparing new measurements of corneal shape and visual acuity with prior records. An optimal shape of the cornea is that shape which permits good correction of the patient's visual defect to obtain functional vision, e.g., that vision acceptable to the patient without molds.

It is contemplated that the patient will progress through a series of molds which will be formed to correspond to the shape of the cornea achieved by use of a prior mold. Once an optimal shape of the cornea has been achieved, as determined by improved vision, the patient will continue to use a "retainer" mold, designed to maintain the functional vision.

The reshaping of the cornea achieved by the molds of the present invention is generally reversible. After abandoning use of the molds for a prolonged period of time, reshaping results could be diminished. However, loss of shape is gradual, and does not occur over generally short periods of time. While retention time of the functional corneal shape will differ with each particular patient, in general it is contemplated that the patient will wear the mold for a period of time each day, for example, about three to 12 hours. Upon removal of the mold, the shape of the cornea and improvements in vision will persist, approximately a few hours to a few days. There are exceptions, including some patients having more long term retention and some that can maintain with night wearing.

The invention may be better understood by reference to the following examples.

EXAMPLES

Example 1: Improvement in myopic patient.

Patient A.D. was first seen wearing daily soft contact lenses to correct myopia. Measurement of the patient's refractive error indicated myopia, the right eye showing 3.25 diopters of refractive error and the left eye 2.50 diopters. The patient's corneal topography was measured and molds were designed to fit the patient's corneas and correct the myopia.

The following measurements and calculations were made:

| PARAMETER | RIGHT EYE | LEFT EYE |
|---|---|---|
| $R_o$ | 7.50 mm | 7.45 mm |
| Refractive Error | 3.25 diopters | 2.5 diopters |
| d | 0.65 mm | 0.50 mm |
| Base curve | 8.15 mm | 7.95 mm |
| $S_a$ | 0.4289322 mm | 0.4317875 mm |
| $S_c$ | 0.3929065 mm | 0.403312 mm |
| $S_a-S_c$ (depression) | 36μ | 29μ |
| Shape Factor | 1.245 | 1.223 |
| Distance from reformed cornea (μ) | | |
| at 0 mm diameter | 36 | 29 |
| at 5 mm diameter | 36 | 29 |
| at 6 mm diameter | 50 | 43 |
| at 7 mm diameter | 77 | 59 |
| 12μ/diopter + $(S_a-S_c)$ | | |
| at 8 mm diameter | 35 | 31 |
| at 9 mm diameter | 36 | 29 |
| at 10 mm diameter | 136 | 129 |

The above coefficients, e.g., desired distance from the cornea at each diameter, were computer fitted to generate the best fit continuous optical curve from which molds were produced. The patient's corneal topography was measured just prior to receipt of the molds fitted to the calculations specified above. Upon receipt, the patient applied the molds to the corneas each morning, wore the molds all day, and removed the molds each night for a period of two weeks. At two weeks, the patients corneal topography was again recorded and refractive error measured (without wearing molds). At two weeks the patient's visual acuity was corrected to 0/0 refractive error or plano, from the previously measured refractive errorr of 3.25/2.50.

I claim:

1. A continuous aspherical optical mold for altering the shape of a patient's cornea comprising:

a generally circular periphery;

an outer, generally convex surface;

an inner, generally concave surface;

wherein said inner concave surface comprises a multi-curved aspherical, continuous radial arc between the center and the periphery of the mold, which radial arc is modified from a central corneal curve determined from a patient's corneal topography to induce a specific desired alteration in the patient's corneal topography, the modified arc having the following characteristics:

a pressure zone having a curvature which is flatter than the central corneal curve, the difference between the curvature of the central corneal curve and the curvature of the pressure zone being determined by the desired alteration in the shape of the patient's cornea, such that when the mold is applied to the cornea, the pressure zone engages the cornea's surface;

a relief zone having a curvature which is steeper than the central corneal curve, the difference between the curvature of the central corneal curve and the relief zone being determined by the desired alteration in the shape of the patient's cornea and correlated to the curvature of the pressure zone, said relief zone being positioned adjacent to said pressure zone such that when the mold is applied to the cornea, the relief zone is raised away from the cornea's surface;

an anchor zone having a curvature which is flatter than the central corneal curve, said anchor zone being positioned between the relief zone and the periphery of the mold such that when the mold is applied to the cornea, the anchor zone engages the cornea's surface; and a second relief zone positioned at the periphery of the lens such that when the mold is applied to a cornea, the second relief zone is raised away from the cornea's surface.

2. The mold of claim 1, having a steepened curvature at the periphery such that when the mold is applied to a cornea, the periphery is raised approximately 80–100 μ from cornea's surface.

3. The mold of claim 1, having a total cross-sectional diameter from periphery to periphery of about 9.0–11.0 mm.

4. The mold of claim 1, having a total diameter from periphery to periphery of about 9.5–10.5 mm.

5. The mold of claim 1, having a total diameter from periphery to periphery of about 10 mm.

6. The mold of claim 1, wherein said pressure zone is positioned at the center of the mold and said relief zone is positioned in an annular ring adjacent to said pressure zone.

7. The mold of claim 6, wherein the diameter of the central pressure zone is approximately 4–7.5 mm.

8. The mold of claim 7, wherein the diameter of the central pressure zone is approximately 4.5–6.0 mm.

9. The mold of claim 8, wherein the diameter of the central pressure zone is approximately 5.0 mm.

10. The mold of claim 7, wherein the relief zone adjacent to the central pressure zone has an annular diameter of about 1–2.5 mm.

11. A continuous, aspherical optical mold for altering the shape of a patient's cornea, comprising:

a generally circular periphery;

an outer, generally convex surface;

an inner, generally concave surface;

wherein said inner concave surface comprises a multi-curved aspherical, continuous radial are defined between the center and the periphery of the mold, which radial arc is modified from a central corneal curve determined from a patient's corneal topography to induce a specific desired alteration in the patient's corneal topography, the modified radial arc having the following characteristics:

a pressure zone positioned at the center of the mold and having a curvature which is flatter than the central corneal curve, the difference between the curvature of the central cornea/curve and the curvature of the pressure zone being determined by the desired alteration in the shape of the patient's cornea, such that when the mold is applied to the cornea, the pressure zone engages the cornea's surface;

a relief zone positioned as an annular ring adjacent to said pressure zone and having a curvature which is steeper than the central corneal curve, the difference between the curvature of the central corneal curve and the curvature of the relief zone being determined by the desired alteration in the shape of the patient's cornea and correlated to the curvature of the pressure zone, such that when the mold is applied to the cornea, the relief zone is raised away from the cornea's surface; and an anchor zone positioned as an annular ring adjacent to the relief zone and between the relief zone and the periphery, and having a curvature which is flatter than the central corneal curve such that when the mold is applied to the cornea, the anchor zone engages the cornea's surface;

and wherein the periphery has a curvature such that when the mold is applied to the cornea, the periphery is raised away from the cornea's surface.

12. A continuous, aspherical optical mold for altering the shape of a patient's cornea, comprising:

a generally circular periphery;

an outer, generally convex surface;

an inner, generally concave surface;

wherein said inner concave surface comprises a multi-curved aspherical, continuous radial arc defined between the center and the periphery of the mold, which radial arc is modified from a central corneal curve determined from a patient's corneal topography to induce a specific desired alteration in the patient's corneal topography, the modified radial arc having the following characteristics:

a relief zone positioned at the center of the mold and having a curvature which is steeper than the central corneal curve, the difference between the curvature of the central corneal curve and the curvature of the relief zone being determined by he desired alteration in the shape of the patient's cornea, such that when the mold is applied to the cornea, the relief zone is raised away from the cornea's surface; and a pressure zone positioned as an annular ring adjacent to said relief zone and having a curvature which is flatter than the central corneal curve, the difference between the curvature of the central corneal curve and the curvature of the pressure zone being determined by the desired alteration in the shape of the patient's cornea and correlated to the curvature of the relief zone, such that when the mold is applied to the cornea, the pressure zone engages the cornea's surface;

wherein the periphery has a curvature such that when the mold is applied to the cornea, the periphery is raised away from the cornea's surface.

13. A method for altering the shape of a patient's cornea comprising:

applying to a patient's cornea a continuous aspherical optical mold, said mold comprising:

a generally circular periphery;

an outer, generally convex surface;

an inner, generally concave surface;

wherein said inner concave surface comprises a multi-curved aspherical, continuous radial arc defined between the center and the periphery of the mold, which radial arc is modified from a central corneal curve determined from the patient's corneal topography to induce a specific desired alteration in the patient's corneal topography, the modified radial arc having the following characteristics:

a pressure zone having a curvature which is flatter than the central corneal curve, the difference between the curvature of the central corneal curve and the pressure zone being determined by the desired alteration in the shape of the patient's cornea, such that when the mold is applied to the cornea, the pressure zone engages the cornea's surface;

a relief zone having a curvature which is steeper than the central corneal curve, the difference between the curvature of the central corneal curve and the curvature of the relief zone being determined by the desired alteration in the shape of the patient's cornea and correlated to the curvature of the pressure zone, said relief zone being positioned adjacent to said pressure zone such that when the mold is applied to the patient's cornea, the relief zone is raised away from the cornea's surface;

an anchor zone having a curvature which is flatter than the central corneal curve, the anchor zone being positioned adjacent to the relief zone and between the relief zone and the periphery of the mold such that when the mold is applied to the patient's cornea, the anchor zone engages the cornea's surface;

wherein said applying causes corneal tissue to be displaced away from areas of the cornea underlying the pressure zone and towards areas of the cornea underlying the relief zone; and wherein the periphery has a curvature such that when the mold is applied to the cornea, the periphery is raised away from the cornea's surface.

14. A method for altering the shape of a patient's cornea comprising:

applying to the patient's cornea a continuous, aspheric optical mold having an inner concave surface with curvature matched to a central corneal curve that is determined from the patient's corneal topography and modified to create a pressure zone, a relief zone, an anchor zone and a periphery, the pressure zone and the anchor zone each having a curvature which is flatter than the central corneal curve the difference between the curvature of the central corneal curve and the curvature of the pressure zone being determined by a desired alteration in the shape of the patient's cornea, and, the relief zone having a curvature which is steeper than the central corneal curve, the difference between the curvature of the central corneal curve and the curvature of the relief zone being determined by the desired alteration in the shape of the patient's cornea and correlated to the curvature of the pressure zone, wherein the pressure zone and the anchor zone engage the corneal surface and the pressure zone exerts a relative pressure to a pre-determined site on the cornea thereby causing a displacement of corneal tissue away from the site of relative pressure, the relief zone accommodating the displaced corneal tissue or volume; and wherein the periphery has a curvature such that when the mold is applied to the cornea, the periphery is raised away from the cornea's surface.

15. The method of claim 14, wherein said pressure zone exerts relative pressure at the center of the patient's corneal dome and thereby reduces or flattens the corneal dome.

16. The method of claim 14, wherein said pressure zone exerts relative pressure at the periphery to mid-periphery of the patient's corneal dome and thereby steepens or heightens the corneal dome.

17. The method of claim 16, wherein said relief zone is positioned about midway between the edge of the flattened pressure zone and the periphery of the mold.

18. A method for treating myopia comprising:

applying to a patient's myopic cornea a continuous, aspheric optical mold having an inner concave surface with a curvature matched to a central corneal curve that is determined from the patient's corneal topography and modified to create a central pressure zone, a relief zone, an annular anchor zone, and a periphery, the pressure zone and the anchor zone each having a curvature which is flatter than the central corneal curve, the difference between the curvature of the central corneal curve and the curvature of the pressure zone being determined by a desired alteration in the shape of the patient's cornea, and, the relief zone having a curvature which is steeper than the central corneal curve, the difference between the curvature of the central corneal curve and the curvature of the relief zone being determined by the desired alteration in the shape of the patient's cornea and correlated to the curvature of the pressure zone, said relief zone being positioned between the pressure and anchor zones, wherein the pressure zone engages the patient's cornea centrally at the corneal dome and exerts a relative pressure thereby causing displacement of corneal tissue away from the corneal dome to flatten the corneal dome and correct the patient's myopia, wherein the relief zone is raised away from the cornea's surface to accommodate corneal tissue or volume displaced by the pressure zone, and wherein the periphery has a curvature such that when the mold is applied to the cornea, the periphery is raised away from the cornea's surface.

19. A method for treating hyperopia comprising:

applying to a patient's hyperopic cornea a continuous, aspheric optical mold having an inner concave surface with curvature matched to a central corneal curve that is determined from the patient's corneal topography and modified to create a central relief zone, and an annular pressure zone, the relief zone having a curvature which is steeper than the central corneal curve, the difference between the curvature of the central corneal curve and the curvature of the relief zone being determined by a desired alteration in the shape of the patient's cornea, and, the annular pressure zone having a curvature which is flatter than the central corneal curve, the difference between the curvature of the central corneal curve and the curvature of the pressure zone being determined by the desired alteration in the shape of the patient's cornea and correlated to the curvature of the relief zone, the pressure zone being positioned adjacent to the central relief zone, wherein the pressure zone engages the periphery to mid-periphery of the corneal dome and exerts a relative pressure thereby causing displacement of corneal tissue or volume toward the corneal dome to steepen the corneal dome and correct the patient's hyperopia.

* * * * *

UNITED STATES PATENT AND TRADEMARK OFFICE
CERTIFICATE OF CORRECTION

PATENT NO. : 5,695,509

DATED : DECEMBER 9, 1997

INVENTOR(S) : EL HAGE

It is certified that error appears in the above-identified patent and that said Letters Patent is hereby corrected as shown below:

Col. 8, line 14: "12.5 mm" should read —1–2.5 mm—

Col. 8, line 26: "(at)" should read —(d)—

Col. 9, line 17: "(0.2)–8.6 mm" should read —(0.2)=8.6 mm—

Col. 9, line 67: "mount" should read —amount—

Col. 10, line 22: "129 lμ" should read —129 μ—

Col. 13, line 51, claim 11: "are" should read —arc—

Col. 13, line 61, claim 11: "cornea/" should read —corneal—

Col. 16, line 61, claim 19: delete "or volume" after the word "tissue"

Signed and Sealed this

Fourth Day of August, 1998

Attest:

BRUCE LEHMAN

*Attesting Officer*  *Commissioner of Patents and Trademarks*